(12) United States Patent
Kiilerich et al.

(10) Patent No.: US 9,101,718 B2
(45) Date of Patent: Aug. 11, 2015

(54) PISTON ROD FOOT

(75) Inventors: Ebbe Kiilerich, Copenhagen NV (DK); Christian Peter Enggaard, Vejby (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/343,149

(22) PCT Filed: Aug. 28, 2012

(86) PCT No.: PCT/EP2012/066696
§ 371 (c)(1),
(2), (4) Date: Apr. 21, 2014

(87) PCT Pub. No.: WO2013/034467
PCT Pub. Date: Mar. 14, 2013

(65) Prior Publication Data
US 2014/0249483 A1     Sep. 4, 2014

Related U.S. Application Data

(60) Provisional application No. 61/532,813, filed on Sep. 9, 2011.

(30) Foreign Application Priority Data

Sep. 6, 2011  (EP) .................................... 11180228

(51) Int. Cl.
*A61M 5/00*     (2006.01)
*A61M 5/315*    (2006.01)
*G01K 11/06*    (2006.01)
*A61M 5/24*     (2006.01)

(52) U.S. Cl.
CPC ....... *A61M 5/31501* (2013.01); *A61M 5/31515* (2013.01); *G01K 11/06* (2013.01); *A61M 5/2429* (2013.01); *A61M 2205/3368* (2013.01); *A61M 2205/583* (2013.01)

(58) Field of Classification Search
CPC ................... A61M 2205/583; A61M 5/31501; A61M 5/31515
USPC ......................................................... 604/232
See application file for complete search history.

(56) References Cited

U.S. PATENT DOCUMENTS

| 4,145,918 A | 3/1979 | Couch et al. |
| 4,191,125 A | 3/1980 | Johnson |
| 6,235,004 B1 | 5/2001 | Steenfeldt-Jensen et al. |
| 2008/0082055 A1* | 4/2008 | Lloyd et al. ................... 604/218 |

FOREIGN PATENT DOCUMENTS

| EP | 774268 A1 | 5/1997 |
| WO | 2007068061 A1 | 6/2007 |
| WO | 2011003979 A1 | 1/2011 |

* cited by examiner

*Primary Examiner* — Kevin C Sirmons
*Assistant Examiner* — Deanna K Hall
(74) *Attorney, Agent, or Firm* — Wesley Nicolas

(57) ABSTRACT

The invention relates to a medical drug delivery apparatus which comprises a cartridge (1) being closed at one end by a membrane (12) and at the opposite end by a movable piston (15). A piston rod foot (1) is provided for transferring the pressure from the piston rod (20) of the drug delivery apparatus and onto the piston (15). The piston rod foot (1) comprises a center part (2) abutting the piston rod (20) and an outer part (3) which center part (2) and outer part (3) are releasable coupled together such that the two (2, 3) can be released when a force above a certain threshold limit is applied to the outer part (3).

8 Claims, 2 Drawing Sheets

PISTON ROD FOOT

CROSS-REFERENCE TO RELATED APPLICATIONS

This application is a 35 U.S.C. §371 National Stage application of International Application PCT/EP2012/066696 (WO 2013/034467), filed Aug. 28, 2012, which claimed priority of European Patent Application 11180228.6, filed Sep. 6, 2011; this application claims priority under 35 U.S.C. §119 of U.S. Provisional Application 61/532,813; filed Sep. 9, 2011.

THE TECHNICAL FIELD OF THE INVENTION

The invention relates to a medical drug delivery apparatus such as an injection pen in which a piston rod moves a piston or plunger forward inside a cartridge and more specifically the invention relates to a piston rod foot or washer for such injection pen.

DESCRIPTION OF RELATED ART

People suffering from diabetes often have to inject themselves with insulin at a daily basis. For this purpose a great number of different pen systems have been developed over the last 30 years. Common for pen injectors is that they contain a container or cartridge containing the liquid drug to be injected. The cartridge is provided with a piston which is moved forward in order to transfer the liquid drug from the injection pen and into the body of the user.

An example of such commercial successful injection pen, the Flexpen® by Novo Nordisk A/S, is given in U.S. Pat. No. 6,235,004. The cartridge (89) as e.g. depictured in FIG. 15-17 contains the liquid drug to be expelled. At the proximal end the cartridge (89) is closed by a rubber piston which is moved forward inside the cartridge (89) by a piston rod (7). In order to transfer and distribute the force from the piston rod (7) to the rubber piston, a piston rod foot (9) is provided between the piston rod (7) and the rubber piston. The piston rod foot is significantly smaller in diameter than the cartridge interior and the piston sliding inside the cartridge.

For prefilled injection pens which is characterized by the fact that they are discarded when the user has used the prefilled amount of drug there is no possibility for the user to return the piston rod to its initial position. The dosing mechanism is usually constructed such that the piston rod can only move in the distal direction since the injection pen is designed only to be used until the prefilled amount of drug has been used. Further, such injection pens are sealed such that the user can not physically obtain contact with the piston rod. In such injection pens the piston rod foot is normally laying loosely between the rubber piston and the piston rod without being attached to any of the two components since this is the easiest way to assemble the injection pen.

Many pharmaceutical companies prescribe that the liquid drug is stored in a refrigerator or another cold storage facility. However, at the same time many of the liquid drugs available are sensible to frost. The liquid drug should therefore be stored above 0 degrees Celsius at all time. Liquid drugs are often contained in a glass cartridge. If such glass cartridge is exposed to frost not only will the liquid drug be damaged but the liquid will also expand its volume. The increased pressure arising from the expansion can cause the glass of the glass cartridge to fracture if no other possibility for expansion is provided.

WO 2007068061 (especially the FIGS. 6 and 7) discloses a container for a liquid drug in which the cap can move axially if the drug is exposed to frost.

In a prefilled injection pen, the piston can not move freely in the proximal direction due to the presence of the piston rod which again is used to expel the liquid drug. However, if the piston rod and the piston foot, which are located between the piston rod and the piston, do not obtain the entire area of the surface of the piston, the peripheral portion of the piston can move proximally thereby surrounding the piston rod foot.

Due to friction between the cartridge wall and the piston during expelling the maximum precision of the size of the injectable dose is obtained if the pressure from piston rod is applied to the piston equally distributed and especially distributed as close to the cartridge wall as possible. However, a large diameter on the piston rod foot, which is preferred in order to distribute the pressure applied at the periphery of the piston, prevents the piston from at least partly move in the proximal direction when exposed to frost thereby increasing the risk for breakage of the glass.

DESCRIPTION OF THE INVENTION

It is an object of the present invention to provide an injection device having a piston rod foot which can transfer the pressure at the periphery of the piston without preventing the piston from moving, at least partly, in the proximal direction should the liquid drug be exposed to frost and expand. It is further an object to provide a build-in freeze-and-thaw indicator indicating to the user whether the drug contained in the injection device has been exposed to frost or not.

The invention is defined in claim 1.

In a first embodiment the piston rod foot comprises a centre part and an outer part releasable connected to the centre part. If the liquid contained in the cartridge is frozen, the liquid will expand. This expansion moves the piston in the proximal direction, as the piston which is usually made from a rubber composition is the weakest link. However, the centre part of the piston rod foot abuts the piston rod which is prevented form movement in the proximal direction due to its coupling with the injection mechanism. As a consequence only the part of the piston lying outside the periphery of the centre part of the piston rod foot can move in the proximal direction. This movement moves the outer part of the piston rod foot proximally out of engagement with the centre part of the piston rod foot.

When the injection device is thawed after having been frozen, the piston will move into its non-frozen position and the outer part of the piston rod foot will remain in the position into which it was moved during freezing. This will provide a slightly lesser precision of the injection device, but the injection device will remain workable. A user inspecting the injection device will be able to visible see if the outer part has been dislocated relatively to the centre part.

The releasable coupling between the centre part and the outer part can be formed in any releasable form making it possible for the two parts to disengage when a certain threshold force is surpassed. The centre part and the outer part can be coupled together by breakable elements such as protrusions which break when a the predetermined threshold force is surpassed.

The piston moves the outer part of piston rod foot axially in the proximal direction when the liquid in the cartridge is exposed to frost. In one example of the invention, the centre part and the outer part have different colours such that a user can easily inspect if the outer part has moved relatively to the centre part.

In a further embodiment, the centre part and the outer can have different coefficients of thermal expansion. If the centre part is made from a first material which retracts more during freezing than a second material from which the outer part can be made, then the two parts can decouple fully or partly in the radial direction during freezing.

The piston rod foot is not necessarily provided as a loose part but can be rotatable or non-rotatable hinged to the piston rod. The inner part of the piston rod foot can also be formed integrally with the piston rod if the injection device e.g. is the type in which the piston rod foot do not rotate relatively to the piston rod during dose ejection.

The present invention also involves the piston rod foot comprising a centre part and an outer part releasable coupled together.

The ability of the two parts to release from each other can be provided in multiple of different ways. Either of the parts can be provided with protrusions engaging similar depressions in the opposite part which protrusion breaks when a certain, predetermined threshold force is surpassed in the axial direction. In a different embodiment, the two parts can be provided with a rim and track coupling which are releasable when a certain threshold force is surpassed. This decoupling can be enhanced by the physical shape of the engagement. If the two parts are made from materials having different thermal expansion a decoupling in the radial direction can be facilitated.

DEFINITIONS

An "injection pen" is typically any kind of injection apparatus having an oblong or elongated shape somewhat like a pen for writing. Although such pens usually have a tubular cross-section, they could easily have a different cross-section such as triangular, rectangular or square or any variation around these geometries. Instead of the term "injection apparatus", the term "drug delivery apparatus" or simply "injection device" is also sometimes used with the same meaning. The broad meaning of the term being any kind of device which is able to transfer a liquid to and/or from a person in a subcutaneous way.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

Correspondingly, the term "subcutaneous" injection is meant to encompass any method of transcutaneous delivery to a subject.

"Cartridge" is the term used to describe the container containing the drug. Cartridges are usually made from glass but could also be moulded from any suitable polymer. A cartridge or ampoule is preferably sealed at one end by a pierceable membrane which can be pierced e.g. by an injection needle. The opposite end is closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. A "piston rod foot" is an element which distributes the force from the piston rod to the movable plunger or piston and is usually located between the piston rod and the movable piston or plunger.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be construed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end pointing towards the needle cannula penetrating the patient whereas the term "proximal end" is meant to refer to the opposite end.

Figure 1:
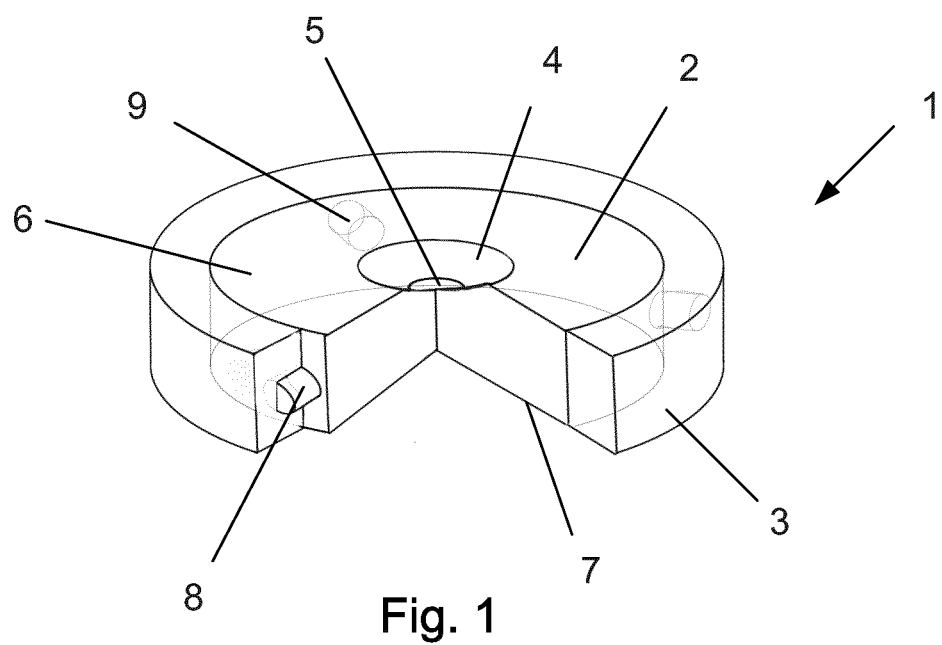
FIG. 1 show an example of the piston rod foot for the drug delivery apparatus according to the invention.

FIG. 1 discloses a piston rod foot 1 for a medical drug delivery apparatus according to the present invention. The piston rod foot 1 comprises a centre part 2 and an outer part 3 which are coupled together. The centre part 2 is in the centre of the proximal surface 6 provided with a circular depression 4 into which a not shown piston rod abut. An opening 5 is provided in the centre of the depression 4. The opposite distal surface 7 abuts the piston 15 (see FIG. 3) during use. The centre part 2 and the outer part 3 are coupled together through a plurality of protrusions 8 in the form of taps engaging similar depression 9. The protrusions 8 are here depicted as being provided on the centre part 2 whereas the depressions 9 are depictured as being provided in the outer part 3. However, this order can be opposite or random.

Figure 2:
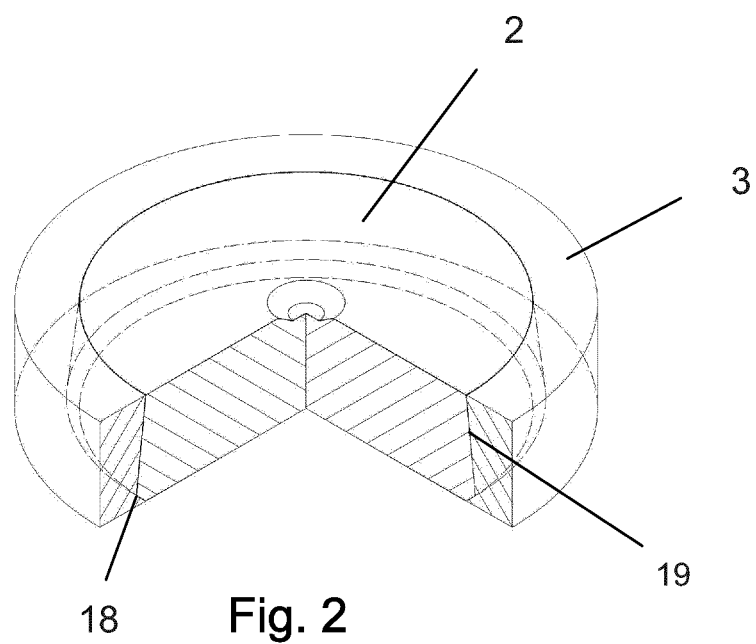
FIG. 2 show a different embodiment of the piston rod foot

FIG. 2 discloses a different embodiment in which the centre part 2 and the outer part 3 engage each other with a V-shaped engagement with one leg in the V being larger than the other such that disengagement are facilitated. The V-shape of the centre part 3 forms a rim 18 circling the centre part 2 and the bottom of the V-shape of the outer part 3 forms a track 19 into which track 19 the rim 18 fits. The centre part 2 and the outer part 3 could also be made from materials having different coefficient of thermal expansion. If e.g. the centre part 2 retracts more than the outer part 3 during freezing, the two parts 2, 3 would fully or partly disengage in the radial direction when exposed to frost.

Figure 3A:
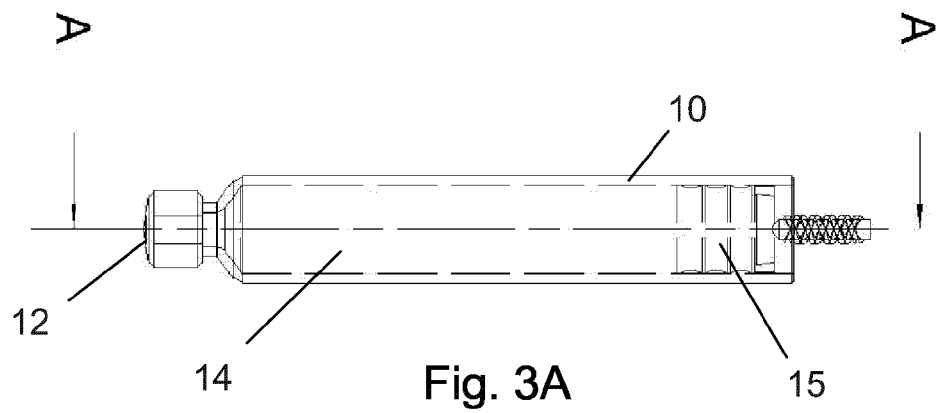
FIG. 3A-D shows different views of the piston rod foot inside the cartridge during freezing and thawing of the liquid drug.
Figure 3B:
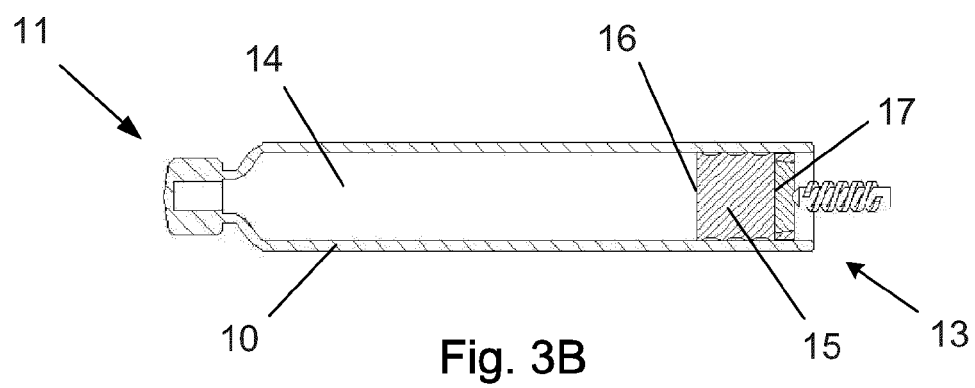
Figure 3C:
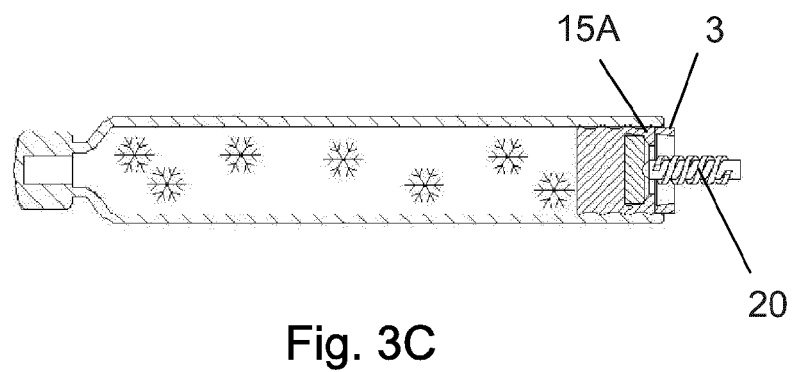
Figure 3D:
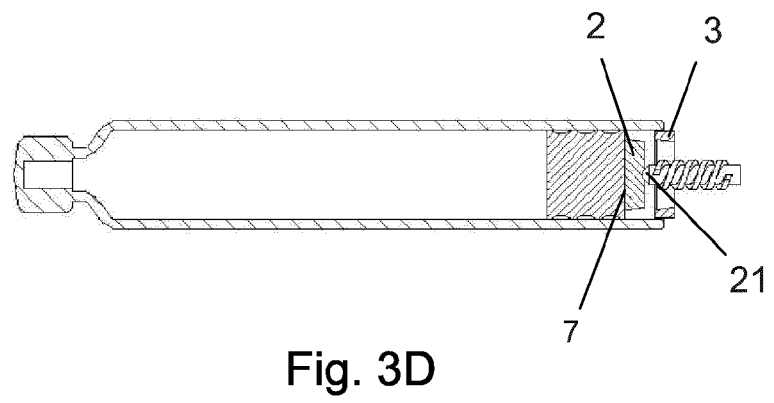

FIG. 3A-D discloses a cartridge 10 for the medical drug delivery apparatus according to the invention. FIG. 3B-D is cross sectional views of A-A of FIG. 3A. The cartridge 10 is at its distal end 11 sealed by a membrane 12 which can be penetrated by a not shown injection needle. At the opposite proximal end 13 the cartridge 10 is closed by the movable piston 15. The piston 15 has a front wall 16 which is in contact with the liquid drug encapsulated in the space 14 between the membrane 12 and the front wall 16 of the movable piston 15. Further, the piston 15 has a back wall 17 abutting the distal surface 7 of the piston rod foot 1.

The piston rod 20 is connected to a not shown injection mechanism which moves the piston rod 20 forward during injection. During injection, the distal end 21 of the piston rod 20 abuts the circular depression 4 provided in the proximal surface 6 of the piston rod foot 1. The distal surface 7 of the piston rod foot 1 is in contact with the piston 15 at its back wall 17 such that a force applied to the piston rod 20 is transmitted to the piston 15 via the contact surface between the piston rod foot 1 and the piston 15.

In FIG. 3B the cartridge 10 is disclosed as not exposed to frost. The centre part 2 and the outer part 3 are coupled together and both abut the piston 15 for maximum precision.

If the liquid drug contained inside the cartridge 10 is exposed to frost as disclosed in FIG. 3C, the liquid drug will expand in the space 14 and force the piston 15, which is usually made from rubber in the proximal direction. However, the centre part 2 which is held in its position by the piston rod 20 can not move proximally why only the portion 15A of the piston 15 being peripheral to the centre part 2 will move proximally and thus surround the centre part 2 as illustrated. This movement will be transferred to the outer part 3 which will follow the proximally movement of the peripheral portion 15A of the piston 15 and move out of engagement with the centre part 2. If the centre part 2 and the outer part 3 are secured by protrusions 8 and depressions 9 as indicated in FIG. 1, the protrusions 8 will break as the outer part 2 is moved proximally.

When the liquid drug is thawed, the piston 15 will transform to its original shape as disclosed in FIG. 3D. The centre part 2 will remain in its position abutting the piston 15 and the outer part 3 will remain in the position into which it was moved during freezing. The user of the device can now continue to use the drug delivery device, however with a little less precision since the piston rod foot 1 no longer abuts the piston 15 at its peripheral portion 15A. At the same time the user will be informed that the liquid drug has been exposed to frost due to the new location of the outer part 3.

Since the cartridge 10 is usually embedded in the housing of the drug delivery device this housing can be provided with a window in the position into which the outer part 3 if moved during freezing such that the user just by inspecting the window can obtain information regarding whether the drug delivery device has been exposed to frost or not. The housing could further be equipped with means for securing the outer part 2 in this proximal position. The outer part 3 is preferably coloured in a distinct colour thereby enhancing the visibility of the outer part 3 in the window.

Some preferred embodiments have been shown in the foregoing, but it should be stressed that the invention is not limited to these, but may be embodied in other ways within the subject matter defined in the following claims.

The invention claimed is:

1. A medical drug delivery apparatus for delivering a liquid drug, comprising
    a cartridge containing the liquid drug to be delivered, the cartridge comprising a distal end and a proximal end connected by an inner wall forming a variable space containing the liquid drug, the distal end being closed by a membrane, and the proximal end being closed by a movable piston having a front-wall and a back-wall, and which piston can be moved toward the distal end of the cartridge by a piston rod thereby decreasing the variable space between the membrane and the piston, and wherein
    a piston rod foot provided between the piston rod and the piston, wherein the piston rod foot comprises a centre part abutting the piston rod and peripheral located outer part which centre part and outer part are releasable coupled together such that
    the outer part of the piston rod foot is axially movable relatively to the centre part in the proximal direction.

2. A medical drug delivery apparatus according to claim 1, wherein the centre part and the outer part are breakable coupled together.

3. A medical drug delivery apparatus according to claim 1, wherein the centre part and the outer part are separated when a force above a certain threshold limit is applied to the outer part.

4. A medical drug delivery apparatus according to claim 1, wherein the centre part and the outer part of the piston rod foot have different colours.

5. A medical drug delivery apparatus according to claim 1, wherein the centre part and the outer part of the piston rod foot are made from materials having different coefficients of thermal expansion such that one of the centre part or outer part retracts more than the other part when exposed to frost.

6. A piston rod foot for a medical drug delivery apparatus, wherein the piston rod foot comprises a centre part and a peripheral located outer part releasably coupled together, such that the outer part of the piston rod foot is axially movable relative to the centre part in the proximal direction.

7. A piston rod foot according to claim 6, wherein the centre part and/or the outer part is provided with a plurality of protrusions engaging similar depression in the centre part and/or outer part.

8. A piston rod foot according to claim 6, wherein the centre part or the outer part is provided with a rim engaging a track in the other of the centre part or outer part.

* * * * *